United States Patent [19]

Shirakura et al.

[11] Patent Number: 4,812,480

[45] Date of Patent: Mar. 14, 1989

[54] COMPOSITION FOR ADMINISTRATION THROUGH A BODY CAVITY

[75] Inventors: Osamu Shirakura, Tokyo; Hideo Kojima; Kiyohisa Ouchi, both of Kumagaya; Sueaki Ishimaru, Gyoda, all of Japan

[73] Assignee: Banyu Pharmaceutical Co., Ltd., Tokyo, Japan

[21] Appl. No.: 137,085

[22] Filed: Dec. 23, 1987

[30] Foreign Application Priority Data

Dec. 27, 1986 [JP] Japan ............................ 61-309177

[51] Int. Cl.$^4$ ...................... A61K 31/19; A61K 31/20
[52] U.S. Cl. ..................................... 514/557; 514/560
[58] Field of Search ................................ 514/557, 560

[56] References Cited

PUBLICATIONS

Chem. Abst. 95-125860y (1981).
International Journal of Pharmaceutics, vol. 19 (1984) pp. 161-167, Molenaar et al: Rectal versus oral absorption of diflunisal in man.
International Journal of Pharmaceutics, vol. 27 (1985) pp. 245-253 Nishihata et al: Sustained-release of sodium diclofenac from suppository.

*Primary Examiner*—Stanley J. Friedman
*Attorney, Agent, or Firm*—Oblon, Fisher, Spivak, McClelland & Maier

[57] ABSTRACT

A composition for administration through a body cavity, which comprises 2',4'-difluoro-4-hydroxy-3-biphenyl carboxylic acid dispersed in a mixture of hydrogenated phospholipids and a fatty base.

1 Claim, No Drawings

COMPOSITION FOR ADMINISTRATION THROUGH A BODY CAVITY

The present invention belongs to a pharmaceutical field. More particularly, the present invention relates to a novel composition for administration through a body cavity, which comprises 2',4'-difluoro-4-hydroxy-3-biphenyl carboxylic acid as an active ingredient having excellent antiinflammatory activity.

2',4'-Difluoro-4-hydroxy-3-biphenyl carboxylic acid of the formula:

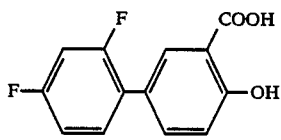

is a pharamaceutically useful compound having excellent antiinflammatory activity, which is commonly called diflunisal.

Heretofore, diflunisal has been used by oral administration. However, it is known that in some cases, diflunisal gives injury to the main absorption site such as gastric mucosa or duodenal mucosa. In order to avoid a side action such as a stimulating action to such an absorption site, an administration route other than the oral administration has been studied. For instance, a rectal dosage form of diflunisal has been known wherein a fatty base is used as the base material (Moolenaar et al., International Journal of Pharmaceutics, Vol. 19, p.161–167, (1984)). It is said that diflunisal is a poorly soluble drug, and when administered to the rectum in the form of a suppository, the drug is hardly soluble in the secretory fluid and hardly absorbable.

Many attempts have been made to improve the absorbability of the drug which has poor absorbability through a mucosal membrane of e.g. the rectum, vagina, nasal cavity or oral cavity. For instance, an attention has been drawn to utilization of coprecipitates with various polymers, utilization of inclusion complexes with e.g. cyclodextrin or incorporation of absorption promoting agents such as surfactants, dimethylformamide, saponin, bile acids or chelating agents (Japanese Unexamined Patent Publications No. 21613/1984, No. 152817/1983, No. 62007/1980, No. 29919/1978 and No. 118510/1982).

The methods of using polymers and cyclodextrin have problems from the viewpoint of the production and the physical characteristics of the products, because they are used in a substantial amount relative to the drug. Further, the polymers have a problem in the compatibility to mucosal membranes. For these reasons, such methods are practically inapplicable to drug formulations. On the other hand, the method of using absorption promoting agents is considered to be useful. However, such agents have relatively strong stimulating activities against mucosal membranes. Therefore, their application to pharmaceutical products is problematic. Further, in the case of a drug such as diflunisal which is hardly soluble and bulky and has extremely poor flowability and which is usually administered in a substantial amount, most of the absorption promoting agents considerably increase the viscosity of the drug formulation by their incorporation, and they present a serious problem for the production or to the physical properties of the final drug formulation such as a suppository. Furthermore, diflunisal powder tends to have electrostatic charge and to adhere to the wall of apparatus, and thus it presents a problem that its handling during the manufacturing process is extremely difficult. Therefore, it has been strongly desired to develop a composition for administration through a body cavity which is easy to prepare and has good compatibility to mucosal membranes and which shows good absorbability of diflunisal.

The present inventors have conducted extensive studies to improve the bioavailability of diflunisal which has poor absorbability from mucosal membranes of e.g. the rectum, vagina, nasal cavity and oral cavity and to obtain a composition which is capable of being readily prepared, and as a result, have found that the absorbability of diflunisal through the mucosal membranes can be improved substantially by incorporating hydrogenated phospholipids to a fatty base. It has been also found that by the addition of hydrogenated phospholipids, the viscosity of the molten mixture for suppository can substantially be lowered during the preparation, and the adhesion of diflunisal powder to the wall of apparatus can substantially be suppressed by the addition of hydrogenated phospholipids. The present invention has been accomplished on the basis of these discoveries.

The present invention provides a composition for administration through a body cavity, which comprises 2',4'-difluoro-4-hydroxy-3-biphenyl carboxylic acid dispersed in a mixture of hydrogenated phospholipids and a fatty base.

Now, the present invention will be described in detail with reference to the preferred embodiments.

In the present invention, the composition for administration through a body cavity includes, in addition to a suppository which is solid at room temperature and capable of readily melting in a body cavity, a dosage form applicable to mucosal membranes of e.g. the rectum, vagine, nasal cavity and oral cavity, such as an ointment or a liquid which is capable of being packed in soft capsules.

Diflunisal as the active ingredient of the composition of the present invention can be prepared by a method disclosed e.g. by J. Hannah et al. in Journal of Medicinal Chemistry, Vol. 21, p.1093 (1978). The composition for administration through a body cavity according to the present invention can be prepared by the fusion method known per se. Namely, it can be prepared by a method wherein a fatty base is heated and melted at a temperature of from 40° to 60° C., then diflunisal powder and hydrogenated phospholipids are added and dispersed therein, and the mixture is poured into a suitable mold, followed by solidification by cooling. The product may be a rectal dosage form or a vaginal dosage form depending upon the shape and the size of the molded product. Further, by using a suitable supporting material, the final product may be formulated into a form suitable for application to the mucosal membranes of the nasal or oral cavity.

Here, with respect to the proportions of the fatty base, diflunisal and the hydrogenated phospholipids, the composition usually comprises 100 parts by weight of the fatty base, from 5 to 25 parts by weight, preferably from 15 to 25 parts by weight, of diflunisal and from 0.1 to 15 parts by weight, preferably from 0.5 to 8 parts by weight, of the hydrogenated phospholipids.

In the present invention, the fatty base may be a vegetable or animal oil or fat such as peanut oil, coconut oil, olive oil, soy bean oil, rape oil, cotton seed oil, sesame oil, corn oil, rice bran oil, camellia oil, cacao butter, wool oil or beef tallow or modified products thereof such as hydrogenated, acetylated or extracted products thereof; a mineral oil such as vaseline, a paraffin, isober or silicone oil; a glycerol ester of a fatty acid having from 6 to 20 carbon atoms, such as Witepsol ® manufactured by Dynamit Nobel Co., Pharmasol ® manufactured by Nippon Oils and Fats Co., Ltd., or Isocacao ® manufactured by Kao corporation; or a $C_2$–$C_8$ lower alkanol ester of a fatty acid, such as isopropyl myristate, butyl myristate, isopropyl linolate, cetyl recinoleate, stearyl recinoleate, diethyl sebacate or diisopropyl adipate.

The hydrogenated phospholipids may be phospholipids of yolk or soy bean hydrogenated to improve oxidation resistance. Such hydrogenated phospholipids usually have an iodine value of from 0 to 80, preferably from 0 to 60. Specifically, commercially available hydrogenated phospholipids such as powder yolk lecithin R-5 ®, R-10 ®, R-20 ® or R-27 ® manufactured by Asahi Chemical Industry Co., Ltd., SLP-white H ® manufactured by True-Lecithin Ind. Co., Ltd., hydrogenated Phosphatidyl Choline ® manufactured by Nippon Oils and Fats Co., Ltd. and Lecinal S-10 ®, S-10M ®, S-10E ®, S-10EX ®, Y-10M ® or Y-10E ® manufactured by Nikko Chemicals Co., Ltd. may be mentioned.

Further, suitable additives, for example, and antioxidant such as butylhydroxyanisol (BHA) or ethylenediaminetetraacetic acid (EDTA), and an antiseptics such as ethyl p-oxybenzoate or propyl p-oxybenzoate, may be incorporated as the case requires.

According to the second aspect of the present invention, there is provided a method of therapy by administering the composition of the present invention in mammalian animals, including human, suffering from inflammation.

The treatment of inflammation in accordance with the method is accomplished by administering to patients the composition described above through a mucosal membrane such as the rectum, vagina, nasal cavity or oral cavity.

Diflunisal may normally be administered at a dosage of from 1 mg to 20 mg/kg body weight per day, preferably from 5 to 15 mg/kg body weight per day.

The above dosage may be given at one time or separately several times a day.

Now, the present invention will be described in further detail with reference to Test Examples. However, it should be understood that the present invention is by no means restricted by these specific Examples. TEST EXAMPLE 1: Test for absorption through rectum

METHOD

A suppository sample was administered to the rectum of a male beagle dog (body weight: about 10kg) fasted for 24 hours. After the administration, the anus was closed with a fingers for a while, and it was confirmed that the suppository was certainly administered. The blood was collected from the front leg vein at predetermined intervals, and the concentration of diflunisal in the blood was monitored with time. The test was conducted by a cross over method by using five animals. The measurement of the concentration of diflunisal in the plasma concentration was conducted by fluorospectrophotometory as described by D.J. Tocco et al. in Drug Metabolism and Disposition, Vol. 3, p.453 (1975).

TEST SAMPLES

Sample A: Commercially available tablets (Dolobid ® 125 mg tablets)
Sample B: Suppository prepared in the same manner as in Example 1 except that no hydrogenated phospholipids were incorporated.
Sample C: Suppository of the present invention as prepared in Example 1.
Sample D: Suppository prepared in the same manner as in Example 1 except that 1% of MGS-A was incorporated instead of the hydrogenated phospholipids.
Sample E: Suppository prepared in the same manner as in Example 1 except that Panacete 800 was incorporated insteaad of the hydrogenated phospholipids.

RESULTS

The results were as shown in Table 1. Namely, the absorption of diflunisal through the rectum by the suppository of the present invention i.e. is comparable to the orally administered tablets (Sample A) and superior to the comparative suppositories i.e. Samples B, D and E.

TABLE 1

|  | Sample A | Sample B | Sample C | Sample D | Sample E |
| --- | --- | --- | --- | --- | --- |
| Administration route | OA | RA | RA | RA | RA |
| Area under the time-concentration curve | 392.2 ± 32.7 | 305.8 ± 56.4 | 360.9 ± 41.4 | 270.0 ± 22.9 | 254.9 ± 19.3 |
| Relative bioavailability (%) | 100 | 78 | 92 | 69 | 65 |
| Maximum plasma concentration (μg/ml) | 76.6 ± 7.7 | 51.1 ± 8.1 | 59.5 ± 7.1 | 45.3 ± 5.2 | 50.4 ± 5.9 |
| Time for reaching the maximum plasma concentration (h) | 1.62 ± 0.47 | 1.54 ± 0.30 | 1.71 ± 0.07 | 2.28 ± 0.57 | 2.12 ± 0.94 |
| Number of animals used | 5 | 5 | 5 | 5 | 5 |

Notes:
OA: Oral administration
RA: Rectal administration
*Average ± standard error

TEST EXAMPLE 2:

Test for absorption through rectum

Method

A test sample was administered through the predetermined administration route to a Sprague-Dawley male rat (body weight: about 250 g) fasted for 24 hours. Then, the blood was collected from the jagular vein at predetermined intervals, and the concentration of diflunisal in the plasma concentration was measured with time. The test was conducted by using five or six animals. The measurement of the concentration of diflunisal in the plasma concentration was conducted in the same manner as in Test Example 1. In order to avoid lowering of the body temperature of the rat during the test, the rat-body temperature was maintained by circulating hot water beneath the plate on which the rat was fixed.

Test samples and administration method

Sample F: Suppository of the present invention obtained in Example 1 containing 125 mg of diflunisal in 650 mg of the sample.
Administration route: rectum
Dose: 50 mg/kg body weight
Sample G: Suspension for oral administration prepared by suspending diflunisal in an amount corresponding to the dose in 2 ml of water.
Administration route: Oral
Dose: 50 mg/kg body weight Results The results were as shown in Table 2. Namely, the rectal absorption of diflunisal by Sample F i.e. the suppository of the present invention is substantially better than the absorption of diflunisal by Sample G i.e. the comparative suspension for oral administration.

TABLE 2

|  | Time (h) | Sample G (oral administration) | Sample F (Rectal administration) |
| --- | --- | --- | --- |
| Plasma | 0.25 | 65.9 ± 19.0(5) | 90.8 ± 6.0(6) |
| concentration | 0.5 | 112.5 ± 27.7(5) | 124.6 ± 12.6(6) |
| (μg/ml) | 1.0 | 158.2 ± 21.5(5) | 162.2 ± 15.8(6) |
|  | 1.5 | 160.1 ± 15.0(5) | 176.9 ± 13.5(6) |
| Average ± | 2.0 | 149.2 ± 7.2(5) | 180.7 ± 9.2(6) |
| standard | 4.0 | 110.5 ± 4.4(5) | 136.0 ± 5.0(6) |
| error | 6.0 | 80.5 ± 3.6(5) | 97.2 ± 8.4(6) |
|  | 8.0 | 67.7 ± 5.6(5) | 78.6 ± 7.7(6) |
| Tmax (h) |  | 1.23 ± 0.32 | 1.47 ± 0.20 |
| Cmax (μg/ml) |  | 158.8 ± 12.8 | 184.7 ± 10.6 |
| AUC(0-8)(μg · h/ml) |  | 853.5 ± 33.7 | 1009.7 ± 42.4 |
| Bioavailability (%) |  | 100 | 118.3 |

Note 1: Dose of diflunisal: 50 mg/kg
Note 2: The numerical value in the parentheses are the number of animals used.

TEST EXAMPLE 3

Method 49.9 g of Pharmasol B-115 ® (manufactured by Nippon Oils and Fats Co., Ltd.) was heated and melted. While mildly stirring the melt, 2.6 g of hydrogenated phospholipids were added and uniformly dispersed. Then, 12.5 g of diflunisal was added thereto, and the mixture was stirred until a uniform dispersion was obtained. On the other hand, a test sample containing no hydrogenated phospholipids was prepared as a comparative sample in the same manner as above. The viscosities of these compositions were measured at 40° C. by means of B8H model rotary viscometer (manufactured by Tokyo Keiki Co., Ltd.) equipped with HH-1 type Spindle. As indices for the evaluation of the viscosities, the yield value and the bingham viscosity were determined.

Results

As shown in Table 3, the yield value and the bingham viscosity were remarkably lowered by the addition of the hydrogenated phospholipids as compared with the sample containing no hydrgenated phospholipids. Thus, it is evident that the hydrogenated phospholipids are effective for lowering the viscosity of the suppository melt. The low viscosity of the melt is very advantageous for the preparation of a desired dosage form.

TABLE 3

Effects of hydrogenated lecithin over the yield value and the bingham viscosity of diflunisal suppository melt (40° C.)

| Hydrogenated phospholipids[a] | Yield value | | Bingham viscosity | |
| --- | --- | --- | --- | --- |
|  | Value (dyn/cm$^2$) | Ratio | Value (dyn · s/cm$^2$) | Ratio |
| None | 47.3 | 1 | 1.16 | 1 |
| Lecinol S-10 ® | 1.0 | 0.02 | 1.02 | 0.88 |
| Lecinol S-10M ® | 8.1 | 0.17 | 1.24 | 1.07 |
| Lecinol Y-10 ® | 13.6 | 0.29 | 1.04 | 0.90 |
| Lecinol Y-10E ® | 21.1 | 0.45 | 1.48 | 1.28 |

[a]Added concentration: 5 weight/weight %

TEST EXAMPLE 4

A suppository of the present invention (Sample H) obtained in Example 1 and a suppository containing no hydrogenated phospholipids (Sample J) prepared in the same manner as in Example 1 were stored under a predetermined temperature condition for 12 months, whereby the dispersion condition of diflunisal was observed by a polarizing microscope.

Results

The results were as shown in Table 4. It is evident that lecinol suppressed the crystal growth of diflunisal in the suppository. Namely, the lecinol-containing suppository of the present invention was found to undergo no substantial crystal growth during the storage at 25° C., whereas the comparative sample containing no lecinol was found to undergo crystal growth slightly during the storage at 15° C. and found to undergo remarkable crystal growth at 25° C.

TABLE 4

Effects of hydrogenated phospholipids over the crystal growth of diflunisal in a suppository

| Storage temperature (°C.) | Sample H | Sample J |
| --- | --- | --- |
| 5 | − | − |
| 15 | − | ± |
| 25 | ± | ++ |
| 30 | ++ | ++ |

*−: No crystal growth observed
±: Slight crystal growth observed
+: Substantial crystal growth observed
++: Extremely high crystal growth observed

TEST EXAMPLE 5:

Test for preventing adhesion to a polyethylene container

Method 2 g of a sample was put in a polyethylene bag (86×194 mm) with its weight (Wa) preliminarily measured. Then, the bag was inflated with air, and the mouth of the bag was closed by an elastic. The bag was thoroughly shaked for 30 minutes. Then, the mouth was opened, and the bag was turned upside down and patted five times to discharge the powder from the bag. Then, the weight (Wb) of the bag was measured. the adhesion rate (%) of diflunisal powder to the polyethylene bag was calculated by the following equation. The results are shown in Table 5.

$$\text{Adhesion (\%)} = \frac{Wb - Wa}{2} \times 100$$

Test Samples

Sample K: Diflunisal bulk
Sample L: Combined powder of diflunisal containing 20% by weight of Lecinol S-10 ®

Results

As shown in FIG. 5, the adhesion of diflunisal powder to the polyethylene bag is substantially prevented by the addition of Lecinol S-10 ®, whereby the handling of diflunisal powder becomes easy.

TABLE 5

| Adhesion rate (%) to a polyethylene bag | | |
|---|---|---|
| Test number | Sample E (%) | Sample F (%) |
| 1 | 13.7 | 1.9 |
| 2 | 13.9 | 1.4 |
| 3 | 6.6 | 2.5 |
| Average | 11.4 | 1.9 |

Now, the present invention is described in further detail with reference to Examples. However, it should be understood that the present invention is by no means restricted to such specific Examples.

EXAMPLE 1

49.9 g of Pharmasol B-115 ® (manufactured by Nippon Oils and Fats Co., Ltd.) was heated and melted, and 2.6 g of Nikkol-Lecinol S-10 ® (iodine value: 9.6) (manufactured by Nikko Chemicals Co., Ltd.) was added thereto and uniformly dispersed under gentle stirring. Then, 12.5 g of diflunisal was added thereto and stirred to obtain a uniform mixture. Then, 650 mg each of the mixture was filled into a film container for molding a suppository, while paying due attention to avoid sedimentation of drug. After the mixture is cooled and solidified, it was taken out from the mold container to obtain a suppository.

EXAMPLE 2

7.677 kg of Pharmasol B-115 ® (manufactured by Nippon Oils and Fats Co., Ltd.) was heated and melted, and 0.4 kg of Nikkol-Lecinol S-10 ® (iodine value: 9.6) (manufactured by Nikko Chemicals Co., Ltd.) was added thereto and uniformly dispersed under gentle stirring. Then, 1.923 kg of diflunisal was added thereto and stirred to obtain a uniform mixture. Then, 1,300 mg each of the mixture was filled into a film container for molding a suppository by means of a filling machine. After the mixture was cooled and solidified, it was taken out from the mold container to obtain a suppository.

EXAMPLE 3

52.2 g of Pharmasol B-115 ® (manufactured by Nippon Oils and Fats Co., Ltd.) was heated and melted, and 0.3 g of Nikkol-Lecinol S-10 ® (iodine value: 9.6) (manufactured by Nikko Chemicals Co., Ltd.) was added and uniformly dispersed under gentle stirring. Then, 12.5 g of diflunisal was added thereto and stirred to obtain a uniform mixture. Then, 650 mg each of the mixture was filled into a film container for molding a suppository, while paying due attention to avoid sedimentation of drug. After the mixture was cooled and solidified, it was taken out from the mold to obtain a suppository.

EXAMPLE 4

49.9 g of Pharmasol B-115 ® (manufactured by Nippon Oils and Fats Co., Ltd.) was heated and melted, and 2.6 g of Nikkol-Lecinol S-30 ® (iodine value: about 30) (manufactured by Nikko Chemicals Co., Ltd.) was added and uniformly dispersed under gentle stirring. then, 12.5 g of diflunisal was added thereto and stirred to obtain a uniform mixture. Then, 650 mg each of the mixture was filled into a film container for molding a suppository, while paying due attention to avoid sedimentation of drug. After the mixture was cooled and solidified, it was taken out from the mold container to obtain a suppository.

EXAMPLE 5

49.9 g of Pharmasol B-115 ® (manufactured by Nippon Oils and Fats Co., Ltd.) was heated and melted, and 2.6 g of Nikko-Lecinol Y-10 ® (iodine value: 8.2) (manufactured by Nikko Chemicals Co., Ltd.) was added and uniformly dispersed under gnetle stirring. The, 12.5 g of diflunisal was added thereto and stirred to obtain a uniform mixture. Then, 650 mg each of the mixture was filled into a film container for molding a suppository, while paying due attention to avoid sedimentation of drug. After the mixture was cooled and solidified, it was taken out from the mold container to obtain a suppository.

EXAMPLE 6

49.9 g of Pharmasol N-145 ® (manufactured by Nippon Oils and Fats Co., Ltd.) was heated and melted, and 2.6 g of Nikkol-Lecinol S-10 ® (iodine value: 9.6) (manufactured by Nikko Chemicals Co., Ltd.) was added and uniformly dispersed under gentle stirring. Then, 12.5 g of diflunisal was added thereto and stirred to obtain a uniform mixture. Then, 650 mg each of the mixture was filled into a film container for molding a suppository, while paying due attention to avoid sedimentation of drug. After the mixture was cooled and solidified, it was taken out from the mold container to obtain a suppository.

EXAMPLE 7

49.9 g of Pharmasol B-115 ® (manufactured by Nippon Oils and Fats Co., Ltd.) was heated and melted, and a powder mixture obtained by preliminarily mixing 2.6 g of Nikkol-Lecinol S-10 ® (iodine value: 9.6) (manufactured by Nikko Chemicals Co., Ltd.) and 12.5 g of diflunisal, was gradually added thereto under gentle stirring, and the stirring was continued to obtain a uniform mixture. Then, 650 mg each of the mixture was filled into a film container for molding a suppository, while paying due attention to avoid sedimentation of drug. After the mixture was cooled and solidified, it was taken out from the mold container to obtain a suppository.

Bioavailability of diflunisal from mucosal membranes of e.g. the rectum, vagina, nasal cavity or oral cavity is improved by the composition for administration through a body cavity according to the present invention, whereby the side effect of diflunisal against gastric mucosa or duodenal mucosa caused by oral administration can be avoided. Further, the hydrogenated phospholipids used as an absorption promoting agent have excellent compatibility to a living body, low toxicity and no substantial stimulating action against mucosal membranes. Thus, the composition for administration through a body cavity according to the present invention is a drug which can be continuously used.

We claim:

1. A composition for administration through a mucosal membrane, which comprises from 5 to 25 parts by weight of 2',4'-difluoro-4-hydroxy-3-biphenyl carboxylic acid, from 0.1 to 15 parts by weight of a hydrogenated phospholipid selected from the group consisting of yolk and soybean hydrogenated to an iodine value of from 0 to 80, and 100 parts by weight of a fatty base selected from the group consisting of vegetable oil, animal oil, fat, mineral oil, glycerol ester of a fatty acid having from 6 to 20 carbon atoms, and a $C_2$-$C_8$ lower alkanol ester of a fatty acid.

* * * * *